United States Patent [19]

Sugihara et al.

[11] Patent Number: 5,238,491
[45] Date of Patent: Aug. 24, 1993

[54] HARDENING MATERIAL FOR MEDICAL AND DENTAL USE

[75] Inventors: Fumihito Sugihara; Takashi Ishii; Tooru Kurihara, all of Osaka, Japan

[73] Assignee: Nitta Gelatin Inc., Osaka, Japan

[21] Appl. No.: 474,766

[22] PCT Filed: Jul. 20, 1989

[86] PCT No.: PCT/JP89/00726

§ 371 Date: Mar. 21, 1990

§ 102(e) Date: Mar. 21, 1990

[87] PCT Pub. No.: WO90/00892

PCT Pub. Date: Feb. 8, 1990

[30] Foreign Application Priority Data

Jul. 23, 1988 [JP] Japan .................. 63-184859

[51] Int. Cl.$^5$ ................................. C09K 3/00
[52] U.S. Cl. ........................ 106/35; 106/161
[58] Field of Search ........... 106/35; 433/228.1; 523/116

[56] References Cited

U.S. PATENT DOCUMENTS

| | | | |
|---|---|---|---|
| 4,677,140 | 6/1987 | Shiotsu | 523/116 |
| 4,776,890 | 10/1988 | Chu | 106/161 |
| 4,780,450 | 10/1988 | Sauk et al. | 514/2 |
| 5,001,169 | 3/1991 | Nathan et al. | 523/113 |
| 5,047,031 | 9/1991 | Constantz | 606/77 |

FOREIGN PATENT DOCUMENTS

| | | |
|---|---|---|
| 0298501 | 1/1989 | European Pat. Off. . |
| 0302847 | 2/1989 | European Pat. Off. . |
| 60-36404 | 2/1985 | Japan . |
| 62-72363 | 4/1987 | Japan . |
| 63-115567 | 5/1988 | Japan . |
| 1068587 | 5/1967 | United Kingdom . |

OTHER PUBLICATIONS

Patent Abstracts of Japan, vol. 12, No. 297 (C-519) (3144), Aug. 12, 1988, & JP, A, 63-66106 (Advance Co., Ltd.) Mar. 24, 1988.
Patent Abstracts of Japan, vol. 11, No. 96 (C-412) (2543), Mar. 26, 1987, & JP, A. 61-246107 (Sankin Kogyo K.K.) Nov. 1, 1986.
The Quintessence, vol. 6, No. 12, Dec. 1987.

*Primary Examiner*—Mark L. Bell
*Assistant Examiner*—Margaret Einsmann
*Attorney, Agent, or Firm*—Armstrong, Westerman, Hattori, McLeland & Naughton

[57] ABSTRACT

This invention relates to a hardening material for medical and dental use which is composed of a powder of calcium phosphate and a hardening liquid.

A subject of the present invention is to provide a hardening material wherein a calcified hard tissue analogous to body hard tissue capable of making chemically a sufficient bond with body hard tissue is formed in a body within relatively short time passage.

To attain the above-described objective, the hardening material for medical and dental use relating to the present invention is composed of a calcium phosphate powder and a hardening liquid and also of at least either one of collagen and/or collagen derivatives in a state of powder or solution, and the calcium phosphate powder contains a powder of α-tricalcium phosphate [α-Ca$_3$(PO$_4$)$_2$]and/or tetracalcium phosphate [Ca$_4$(PO$_4$)$_2$O] as an essential component and the hardening liquid comprises at least one acid selected from inorganic acids and acetic acid.

1 Claim, No Drawings

HARDENING MATERIAL FOR MEDICAL AND DENTAL USE

DESCRIPTION

1. Technical Field

This invention relates to hardening materials for medical and dental use which are used as materials for medical or dental treatment of periodontal diseases, root canal sealing, broken bone filling, hard tissue adhesion and so on.

2. Background Art

As a therapeutic material for periodontal diseases, for example, a mixture of particles of hydroxyapatite (hereinafter referred to as ⌜HAp⌟) or β-tricalcium phosphate [β-$Ca_3(PO_4)_2$] (hereinafter referred to as ⌜β-TCP⌟) and a collagen solution was proposed (the Quintessense, 6(12), 1987).

On the other hand, as root canal sealing materials, for examples, a point such as a guttapercha point or a silver point has been used in combination with a paste agent such as calcium hydroxide or with a cement such as zinc oxide eugenol. A self-setting type apatite cement has also been proposed, which is obtained by mixing tetracalcium phosphate [$Ca_4(PO_4)_2O$] (generally referred to as ⌜4CP⌟ or ⌜TeCP⌟ and hereinafter as ⌜4CP⌟) containing barium apatite with a diluted phosphoric acid solution. The mixture is hardened at a neutral region, and the hardened substance has X-ray opaque character (a contrast character) (YUTAKA DOI et al., "J. J. Dent. Mat.", Special 11, 1988).

Regarding the above-described materials for medical treatment of periodontal diseases, its leakage can be prevented to a certain degree by adhesiveness of collagen to HAp or β-TCP but a chemical binding with tooth cementum can not be expected.

On the other hand, although a guttapercha point, which has been used in combination as a filling material for root canal, shows almost no cytotoxicity and no facile transformation in a body, it is not expected to have osteoconduction because it is a natural resin like gum.

Furthermore, with the above-described self-setting type apatite cement it is possible to form a calcified hard tissue and so hopeful as a filling material for root canal, but it is not possible to make a chemically sufficient binding with hard tissue. Therefore, the filling and bonding are not enough, so that there exists a problem that a gap is formed between the apatite cement and hard tissue.

Thus, a subject of the present invention is to provide a hardening material for medical and dental use wherein a calcified hard tissue analogous to body hard tissue capable of making a chemically sufficient bond with body hard tissue is formed in a body within relatively short time passage.

Disclosure of Invention

To attain the above-described subject, the hardening materials for medical and dental, use relating to the present invention are composed of a calcium phosphate powder and a hardening liquid and also of at least either one of collagen and/or collagen derivatives (hereinafter referred to as ⌜collagen⌟) in a state of powder or solution; the calcium phosphate powder contains a powder of α-tricalcium phosphate (α-$Ca_3(PO_4)_2$) (hereinafter referred as to ⌜α-TCP⌟) and/or 4CP as an essential component and the hardening liquid comprises at least one acid selected from inorganic acids and acetic acid.

The hardening materials for medical and dental use relating to the present invention, in addition to the above description, further comprises that collagen requires for fibrillation a time longer than 8 minutes under physiological conditions.

In the hardening materials related to the invention when the powder and liquid are mixed, the α-TCP and 4CP in the powder are hydrated to form amorphous calcium phosphate [$Ca_3(PO_4)_2 \cdot nH_2O$] (hereinafter referred to as ⌜ACP⌟) and octacalcium phosphate [$Ca_8H_2(PO_4)_6 \cdot 5H_2O$] (hereinafter referred to as ⌜OCP⌟), respectively. Accompanied with this, pH of the mixture becomes to a neutral region and hence the collagen dissolved in the liquid forms fibrils. Then, the ACP and OCP cohere to the collagen fibrils under this condition and then transform into HAp and/or apatite with progression of hardening. The α-TCP and 4CP may form themselves directly into HAp and/or apatite under different conditions, not necessarily through such a HAp precursor as ACP and OCP. The hardened body formed resembles the hard tissues and combines chemically with hard tissues through the collagen fibrils and with growing crystals of HAp and/or apatite. Besides, when collagen is used as a constituent of the powder and the powder and the liquid are mixed, it at once dissolves in the mixture and then forms fibrils upon hardening.

In hardening materials relating to the present invention when a powder and liquid are mixed and milled, it is surely prevented that fibrillation of collagen proceeds to hardening of calcium phosphate. Because of this, surely obtainable is complex in which collagen fibrils chemically combine with HAp and/or apatite.

As a part or a whole of a calcium phosphate powder, either one or both of α-TCP and/or 4CP are used. For a remaining part of the powder, HAp, apatite, apatite carbonate, β-TCP, calcium hydrogenphosphate dihydrate ($CaHPO_4 \cdot 2H_2O$) (hereinafter referred to as ⌜DCPD⌟), barium apatite, and OCP are used. If HAp and/or apatite (hereinafter simply referred to as ⌜HAp⌟) are used as a calcium phosphate powder, HAp acts as a hardening accelerator and becomes a crystal species for growing crystals of HAp, so that leakage of calcium phosphate is more easily prevented.

It is preferred that either one or both of α-TCP and/or 4CP is 40~100% (w/w) against the total weight of calcium phosphate powder. If less than this amount, OCP and HAp themselves, which are precursors of HAp, become hard to grow and there is sometimes caused a problem in that coagulation and hardening are delayed.

In a case where α-TCP and 4CP are used in combination, a combination proportion of the both is preferred to be a mole ratio of 2:1 or this neighboring mole ratio (for example, 1.7:1~2.3:1). If deviated from these combination proportion, there is sometimes a problem in that it is hard for a transformation reaction to take place.

The powder is preferred to have an average particle diameter of 1~50 μm. If deviated from this range, there is sometimes a problem in that an operation of mixing and milling becomes difficult.

As 4CP, for example, can be used the one which is prepared by baking a composition of γ-$Ca_2P_2O_7$ and $CaCO_3$ in a mole ratio of 1:2 at a temperature of 1300°

C. or more followed by pulverizing. Also, the ones prepared by other methods can be used.

As α-TCP, for example, can be used one which is prepared by baking a composition of γ-$Ca_2P_2O_7$ and $CaCO_3$ in a equal mole ratio at a temperature of 1200° C. or more followed by pulverizing. Also, the ones prepared by other methods can be used.

As a hardening liquid is used at least one kind of liquid selected from inorganic acids and acetic acid. As the previously-described inorganic acids, for examples, are used hydrochloric acid, nitric acid, and phosphoric acid. As phosphoric acid is used orthophosphoric acid ($H_3PO_4$) and pyrophosphoric acid ($H_4P_2O_7$). The acid concentration of a hardening liquid is preferred to be adjusted to a pH of 1~6. If pH is deviated from this range, fibrillation of collagen takes place in advance of coagulation and a hardening reaction, and collagen fibrils are separated, so that there is sometimes a problem in that coagulation and hardening does not take place. Besides, the hardening liquid is a solution of watersolvent or an aqueous solution.

In the present invention, collagen is used in a powder state or a solution state. This choice is properly determined according to a technology. In either case, when a powder component and a liquid component are mixed and milled, it is required that collagen once dissolves and filbrillation takes place accompanied with hardening. When being mixed and milled, if collagen is already fibrils, the above-described problem is encountered.

In a case that where collagen is used in a solution state, it is usable by dissolving it in the previously-described hardening liquid or by preparing a collagen solution independent of the hardening liquid. In the case of dissolving collagen, an aqueous solution is prepared by dissolving it in water. In the case that collagen is used in a powder state, it is used by mixing with the previously-described calcium phosphate or by not mixing with this phosphate.

The usage proportion of collagen is prefered to be 0.02~100 weight parts against 100 weight parts of a calcium phosphate powder. If the usage proportion of collagen is deviated from this range, there is sometimes encountered a problem that a chemical binding at an interface between a coagulating, hardening body and the hard tissue of a living body becomes weak and the operation of mixing and milling becomes difficult.

As collagen is used one or two kinds or more selected from collagen treated with alkali, collagens solubilized by treatment with neutal salts or enzyme, and their derivatives.

In general, collagen undergoes fibrillation in a very short time under physiological conditions (for example, pH of 7.0~7.4, temperature of 36°~37° C., a salt concentration of 0.14M). Because of this, in materials for medical and dental use relating to the invention in claim 1, at least one in a group of collagen and collagen derivatives undergoes cohesion and sometimes separates from a coagulated body of calcium phosphate. If this separation takes place, it is not possible to get a composition where HAp and collagen chemically combines. Thus, to get this composition, it is preferred to use collagen not leading to fibrillation within a very short time, for example, the above-described collagen. However, as long as it is a collagen species having this kind character, the collagen is not limited to type I collagen, and the type II collagen and type IV collagen can be also used. The above-described very short time indicates 8 minutes, more preferably about 10 minutes.

According to the present invention when fibrillation of collagen and coagulation and hardening of calcium phosphate procceds in parallel or in almost parallel, it is possible to obtain a hardened body wherein a collagen fibril and a calcium phosphate hardened material coalesce into one body. Thus, the hardened body obtained combines chemically and sufficiently with a living body hard tissue.

The above-described hardening liquid, besides collagen and the previously-described acids, may be used with addition, if nessesary, of polysaccarides such as alginic acid, carrageenan, pectin, xanthan gum, locust-bean gum, and jellan gum, which converts into a gel by a calcium ion, and mucopolysaccharide, chitin, and chitosan.

In the present invention, the composition proportion of a calcium phosphate powder and a hardening liquid is preferred to be adjusted in a weight ratio of 0.1 to 3.0 (g/g) of a calcium phosphate powder and a hardening liquid. If deviated from this range, there is sometimes caused a problem that coagulation and hardening does not take place and operation of mixing, milling, and filling becomes difficult.

The hardening materials relating to the present invention wherein a powder component and a liquid component are mixed and milled at a desired temperature, for example, a room temperature to transform into a slurry or a paste, which are applied, injected, or filled for a treatment part. The slurry and paste under physiological conditions, for example, undergo the chemical reactions of (a)~(c), described below, forming a complex and thus, they coagulate and harden in a neutral region (for example, pH 7.0~7.4).

In addition, they make a chemically sufficient binding with hard tissues. When used as hardening materials for medical and dental use relating the present invention, the formation of a hardening body analogous to hard tissues, which coalesces into one body with hard tissues, takes place within a relatively short period, for instance, during a few days or 14 days.

(a) In a case where, as calcium phosphate powder, 4CP and DCPD are used:

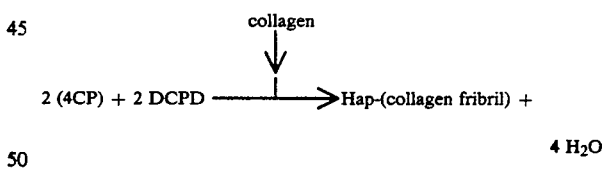

(b) In a case where as a calcium phosphate powder, α-TCP is used:

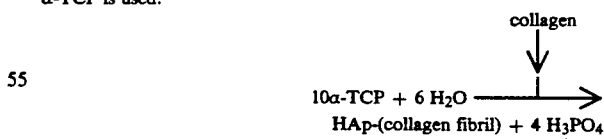

(c) In a case where, as a calcium phosphate powder, α-TCP and 4CP are used in combination:

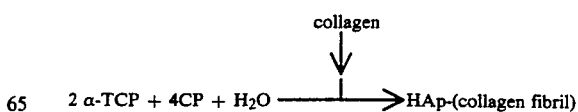

In the above-described (a) reaction system, when a calcium phosphate powder contains barium apatite too, a HAp-collagen complex grows as crystals taking barium apatite as a seed crystal and then, coalesces into one body. Since this complex has a Roentgen contrast character, a binding process with hard tissues in a treatment part can be easily confirmed.

HAp and collagen fibril chemically coalesce into one body and, together with growing of apatite crystals of a hardened body formed at an intersurface between the coalesced one and hard tissues, collagen makes a circumstance to multiplicate regularly bone cells, so that the HAp-collagen complex makes a chemically sufficient binding with hard tissues and leakage of calcium phosphate at a treating part is prevented.

BEST MODE FOR CARRYING OUT THE INVENTION

Hereinafter, although are concretely shown examples and examples for comparison for hardening materials relating to the present invention, this invention is not limited to the below-described examples. Incidentally, the collagen used in the below-described examples and examples for comparison 1 and 2 did not undergo fibrillation within 10 minutes under physiological conditions (pH7.4, temperature 37° C., salt concentration 0.14M). The collagen used in example for comparison 3 undergos fibrillation during about 2 minutes under the same physiological conditions. Also, the powder used had an average particle diameter in a range of 1~50 μm.

EXAMPLE 1

A Cellmatrix LA (collagen solubilized by enzyme, a product from Nitta Gelatin Inc.) was lypophilized. A hardening material for medical and dental use was prepared by being composed of 60 weight parts of an equal molar composition powder of α-TCP and DCPD, and 40 weight parts of an aqueous hydrochloric acid solution (concentration of hydrochloric acid was 50 mM) containing 2% (w/w) of the above lypophilized material.

EXAMPLE 2

A Cellmatrix LA was lypophilized. A hardening material was prepared by being composed of 60 weight parts of an equal molar composition powder of 4CP and DCPD, and 40 weight parts of an aqueous orthophosphoric acid solution (concentration of orthophosphoric acid was 20 mM) containing 2% (w/w) of the above lypophilized material.

EXAMPLE 3

A hardening material was prepared by being composed of 60 weight parts of a composition powder of α-TCP and 4CP in a 2:1 molar ratio and 40 weight parts of an aqueous hydrochloric acid (concentration of hydrochloric acid was 50 mM) containing 2% (w/w) of collagen treated with alkali.

The collagen treated with alkali, used here, was obtained by treating of abstraction from a purified collagen material with a $Na_2SO_4$-saturated about 5% (w/w) aqueous sodium hydroxide solution followed by adjusting at pH 7 with hydrochloric acid, washing with water, and lypophilization.

EXAMPLE 4

A hardening material was prepared by being composed of 60 weight parts of a composition powder of 4CP and DCPD in a 1:4 molar ratio and 40 weight parts of an aqueous acetic acid solution (concentration of acetic acid was 50 mM) containing 2% (w/w) of collagen treated with alkali.

The collagen treated with alkali, used here, was the same as used in the previous example 3.

EXAMPLE FOR COMPARISON 1

A Cellmatrix LA was lypophilized. A material was prepared by being composed of 60 weight parts of β-TCP powder and 40 weight parts of an aqueous hydrochloric acid solution (concentration of hydrochloric acid was 50 mM) containing 2% (w/w) of the above lypophilized material.

EXAMPLE FOR COMPARISON 2

A hardening material was prepared by being composed of 60 weight parts of a powder of an equal molar composition of 4CP and DCPD and 40 weight parts of a 20 mM aqueous orthophosphoric acid.

EXAMPLE FOR COMPARISON 3

A Cellmatrix IA (acid-soluble collagen made by Nitta Gelatin Inc.) was lypophilized. A hardening material was prepared by being composed of 60 weight parts of an equal molar composition powder of α-TCP and DCPD, and 40 weight parts of an aqueous citric acid (concentration of citric acid was 1 mM) containing 2% (w/w) of the above lypophilized material.

For each of the hardening materials in the above-described examples and examples for comparison, the powder and the liquid were mixed and milled at room temperature and subjected to an initial hardening at 37° C. for about 30 minutes. This initially hardened material was soaked for 24 hours in a physiological salt water buffered by phosphoric acid of 37° C. (hereinafter referred to as PBS ) and then, analyzed with a powder X-ray diffraction analysis, a scanning electron microscope, and an infrared absorption spectra. Also, the previously-described initially hardened material was filled by injecting into a broken bone part in the femur of a rabbit and, two weeks later, a pathologic tissue observation was carried out with a non-deliming sample. Results are shown in table 1.

TABLE 1

| | Product after soaking for 24 hours in PBS at 37° C. | Observation two weeks later since injected and filled in a femur-broken part of rabbit |
|---|---|---|
| Example 1 | OCP and collagen fibrils coalescing into one body. | A number of bone cells existed in an interface between filled material and bone tissue and, through apatite-collagen grown as crystals, it combined with bone tissue. Furthermore, a new-born bone was formed in the inside of filled materials. |
| Example 2 | HAp and collagen fibrils coalescing into one body. | A number of bone cells existed in an interface between filled material and bone tissue and, through apatite-collagen grown as crystals, it combined with bone tissue. Furthermore, a new-born bone was formed in the inside of filled materials. |

TABLE 1-continued

| | Product after soaking for 24 hours in PBS at 37° C. | Observation two weeks later since injected and filled in a femur-broken part of rabbit |
|---|---|---|
| Example 3 | HAp and collagen fibrils coalescing into one body. | A number of bone cells existed in an interface between filled material and bone tissue and, through apatite-collagen grown as crystals, it combined with bone tissue. Furthermore, a new-born bone was formed in the inside of filled materials. |
| Example 4 | OCP and collagen fibrils coalescing into one body. | A number of bone cells existed in an interface between filled material and bone tissue and, through apatite-collagen grown as crystals, it combined with bone tissue. Furthermore, a new-born bone was formed in the inside of filled materials. |
| Example for Comparison 1 | No coagulation and hardening, and β-TCP remains. | Newborn bone was, in part, formed around filling materials. |
| Example for Comparison 2 | HAp | Newborn bone was, in part, formed around filling materials. |
| Example for Comparison 3 | Collagen fibrils and coagulated materials composed of HAp and ACP were separated. | A light degree of inflammatory reaction was seen around filling materials. |

As seen in table 1, the hardening materials in the examples afforded a product which is formed by coalescence of OCP (which is a precursor of HAp.) or HAp, and collagen fibrils into one body. In the example for comparison 1, β-TCP remained without coagulating and hardening. In the example for comparison 2, HAp was formed. In the example for comparison 3, a coagulation product composed of HAp and ACP were separated from collagen fibrils and the hardening was not enough. In viewing an inside of living body, all the examples showed a new-born bone forming to an inside of the filled material and combining with bone, whereas the examples for comparison 1 and 2 showed only slight formation of a new-born bone around the filled material and the binding with bone is not sufficient. In the example for comparison 3, a light degree of inflammatory reaction is seen and binding with body bone is not sufficient.

The hardening materials for medical and dental use relating to the invention claimed in claim 1 and 2, as described above, are those which form calcified hard tissue that is analogous to living body hard tissues and makes a sufficiently chemically bound combination with hard tissues.

The hardening materials relating to the invention claimed in claim 2, moreover, are those where chemical bindings take place more surely with hard tissues.

INDUSTRIAL APPLICABILITY

The hardening materials relating to the present invention can be used as filling materials and bonding agents for a living body hard tissue in a place where mechanical strength is not needed, for examples, those that can be used as materials for medical treatment of periodontal diseases, sealing materials for root canal, filling materials for a broken bone, and bonding agents for hard tissue etc.

We claim:

1. Hardening materials for medical and dental use, comprising a powder of calcium phosphate, a hardening liquid and at least one of collagen and a collagen derivative, wherein said calcium phosphate powder is composed of a powder of at least one of α-tricalcium phosphate and tetracalcium phosphate, said hardening liquid is a solution of at least one acid selected from inorganic acids and acetic acid, and wherein said collagen and collagen derivatives are in a non-fibrillar state and are selected from those which require eight minutes or more to undergo fibrillation under physiological conditions.

* * * * *